United States Patent [19]

Merli et al.

[11] Patent Number: 4,939,295
[45] Date of Patent: Jul. 3, 1990

[54] PROCESS FOR THE PREPARATION OF INTERMEDIATES FOR THE SYNTHESIS OF DILTIAZEM

[75] Inventors: Valeriano Merli, Occhiobello; Giorgio Sagramora, Padova; Giorgio Soriato, Caldiero, all of Italy

[73] Assignee: Zambon Group S.p.A., Vicenza, Italy

[21] Appl. No.: 384,438

[22] Filed: Jul. 25, 1989

[30] Foreign Application Priority Data

Jul. 26, 1988 [IT] Italy .................. 21478 A/88

[51] Int. Cl.⁵ .............................................. C07B 57/00
[52] U.S. Cl. ...................................... 562/401; 562/431
[58] Field of Search ................................ 562/401, 431

[56] References Cited

U.S. PATENT DOCUMENTS 4,209,638  6/1980  Nicholson et al. ............. 562/401
4,723,033  2/1988  Erickson ........................... 560/56
4,786,731  11/1988  Russell .............................. 544/354

Primary Examiner—Werren B. Lone
Assistant Examiner—Vera C. Clarke
Attorney, Agent, or Firm—Stevens, Davis, Miller & Mosher

[57] ABSTRACT

A process for the preparation of (2S,3S)-threo-2-hydroxy-3-(2-aminophenylthio)-3-(4-methoxyphenyl)-propionic acid by resolution of the racemic mixture is described.

The resolution is carried out by using as resolving agent (1S,2S)-threo-1-phenyl-2-amino-1,3-propanediol or (1S,2S)-threo-1-(4-methylthiophenyl)-2-amino-1,3-propanediol.

7 Claims, No Drawings

PROCESS FOR THE PREPARATION OF INTERMEDIATES FOR THE SYNTHESIS OF DILTIAZEM

The present invention relates a process for the resolution of (2S,3S)-threo-2-hydroxy-3-(2-aminophenylthio)-3-(4-methoxyphenyl)-propionic acid from mixtures with its (2R,3R)-threo enantiomer. Said compound is an intermediate for the preparation of (+)cis-3-acetoxy-5-(2-dimethylaminoethyl)-2,3-dihydro-2-(4-methoxyphenyl)-1,5-benzothiazepin-4(5H)-one, a drug having coronary vasodilator activity known with the International Common Name of Diltiazem (Merck Index, X Edition, 1983, no 3189, page 466).

Several methods of synthesis for obtaining racemic mixtures of the threo-2-hydroxy-3-(2-aminophenylthio)-3-(4-methoxyphenyl)-propionic acid are known, for example those described in the Euorpean patent application No. 98892 (in the name of Tanabe) and in the references therein mentioned.

Only one of the enantiomers and in particular the (2S,3S)-threo is useful for the preparation of Diltiazem. Therefore it is necessary to seperate it by resolution of the mixture.

Some other processes for the resolution are also described in literature and from among them one which uses (+)-alpha-phenethylamine as resolving agent (Japanese patent application No. 59-231065 in the name of Tanabe).

We have not found a method for resolution particularly convenient from the industrial viewpoint that affords the desired enantiomer with high yields e high purity and uses resolving agents of very low cost.

It is therefore the object of the present invention a process for the separation of the (2S,3S)-threo enantiomer of 2-hydroxy-3-(2-aminophenylthio)-3-(4-methoxyphenyl)-propionic acid from the racemic mixture, consisting in using as resolving agent an amount substantially in the molar ratio of 0.5, with respect to the mixture to be resolved, of (1S,2S)-threo-1-aryl-2-amino-1,3-propanediol of the formula I below reported, in the presence of an amount substantially in the molar ratio of 0.5 with respect to the mixture to be resolved, of an alkaline hydroxide in an aqueous or aqueous-alcoholic solvent.

The used resolving agents can be represented by the following formula

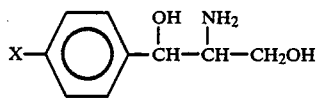

(I, threo 1S,2S)

wherein X=H, CH$_3$S, NO$_2$, CH$_3$SO$_2$.

The compound wherein H=CH$_3$S is known as L-threo-thiomicamine and it is a by-product in the synthesis of thiamphenicol.

Therefore it is available in relevant amounts at practically negligeable prices.

The resolving agent is used in a molar ratio of 0.5 with respect to the enantiomeric mixture and namely in a molar ratio of 0.5:1 or in slight default (5–10%) for example in a ratio of 0.45:1. The alkaline hydroxide is preferably sodium hydroxide or potassium hydroxide and it is also used in a molar ratio of 0.5:1 with respect to the resolving mixture or in slight excess (5–10%), for example in a ratio of 0.55:1.

The solvent can be water or a lower alcohol, for example methanol, ethanol, isopropanol, n.butanol, it can be alcohol in admixture with water.

For economic reasons it is preferable to use water as solvent because it does not afford differences in the yield and in the purity of the desired product.

The resolution is carried out by heating at reflux the reaction mixture up to complete dissolution, then by cooling slowly up to the temperature at which starts the crystalization of the salt of (2S,3S)-threo-2-hydroxy-3-(2-aminophenylthio)-3-(4-methoxyphenyl)-propionic acid with (1S,2S)-threo-1-aryl-2-amino-1,3-propanediol. The salt is then separated and, if necessary, recrystallized.

In agreement with the usual resolution procedures, the precipitation can be started up by adding a small quantity of the desired salt.

The (2S,3S)-threo-2-hydroxy-3-(2-aminophenylthio)-3-(4-methoxyphenyl)-propionic acid is isolated by treatment of the salt with mineral acids in aqueous environment.

Alternatively, the salt can be directly used as such in the subsequent reactions for the synthesis of Diltiazem.

The above reactions comprise the cyclization to cis-3-hydroxy-2-(4-methoxyphenyl)-2,3-dihydro-1,5-benzothiazepin-4-5H-one, the acetylation of the hydroxy group in position 3 and the alkylation of the nitrogen atom in 5 position for introducing the N-(2-dimethylaminoethyl) group, alternatively the two last reactions can be carried out in inverted order.

These reactions can be carried out by known procedures, such as for example the processes described in the Japanese patent applications No. 60-64974 in the name of Kawashima and No. 60-155168 in the name of Tobiashi or in the European patent application No. 81234 in the name of Tanabe.

In a preferred embodiment, the resolution object of the present invention is carried out by using as resolving agent (1S,2-S)-threo-1-(4-methylthiophenyl)-2-ammino-1,3-propanediol and in a molar ratio of 0.45:1 with respect to the mixture to be resolved, sodium hydroxide in a molar ratio of 0.55:1 with respect to the mixture to be resolved and water as solvent; the mixture is heated at about 100° C. up to complete dissolution and then is cooled in 2–5 hours at a temperature of about 30°–40° C.

This temperature is maintained up to the end of the precipitation and the precipitated salt is collected by filtration. If desired, the salt can be recrystallized for example by water. By operating in such manner the desired product is obtained with 70–80 % yield and with about 98% optical purity.

With respect to the known methods, the process of the invention shows various relevant advantages from the point of view of the industrial application.

The main of these is the use of a resolving agent of negligeable cost being a by-product of other industrial synthesis.

That allows to avoid the recovery of the resolving agent, but if it should be done, there is besides the advantage of an easy recovery in that the above cited 2-amino-diols are solid at room temperature, contrary to other resolving agents such as the (+)-alpha-phenethylamine.

With the aim to better illustrate the present invention the following example are now given.

EXAMPLE 1

Threo-2-hydroxy-3-(2-aminophenylthio)-3-(4-methoxyphenyl)-propionic acid (40 g; 0.1252 mol) as equimolecular mixture of (2R,3R) and (2S,3S) enantiomers, solid NaOH at 98% (2.81g; 0.06884 mol, molar ratio 0.55:1 with respect to the derivative of the threo proprionic acid), (1S,2S)-threo-1-(4-methylthiophenyl)-2-amino-1,3-propanediol (S,S-threo-thiomicamine) (12.02 g; 0.05643 mol, molar ratio 0.45:1 with respect to the derivative of the threo propionic acid) and water (720 g) were charged in 1 l reactor equipped with thermometer and reflux condenser.

The mass was reflux heated and kept so for 1 hour. A limpid solution is obtained at 97° C. The heating was removed and the temperature was decreased in such a way as to bring it at 35° C. in 5 hours. The crystallization began at 76° C.

After one night at 35° C. it was filtered and washed with 50 ml of water at 35° C. and then twice with water at room temperature to obtain the curde salt of (2S,3S)-threo-2-hydroxy-3-(2-aminophenylthio)-3-(4-methoxyphenyl)-propionic acid with S,S-threo-thiomicamine.

A dried sample of the crude salt had $[\alpha]_D^{23} = +308.92°$ (c=0.5% in $CH_3OH$).

The wet product was dissolved in refluxing water (616 ml).

The solution was left to cool spontaneously at room temperature (about 20° C.) and it was filtered and washed with water.

The filtrate was dried under vacuum at 65° C. to obtain the desired salt (25.3 g; $[\alpha]_D^{23} = +319.26°$, c=0.5% in $CH_3OH$).

EXAMPLE 2

By working in a way analogous to that described in example 1 27.52 g of crude salt (82.36% yield) were obtained with $[\alpha]_D^{23} = +308.85°$ (c=0.5% in $CH_3OH$).

The salt was diluted in water and treated at warm with hydrochloric acid.

The precipitate so formed was washed with water and dried for obtaining the (2S,3S)-threo-2-hydroxy-3-(2-aminophenylthio)-3-(4-methoxyphenyl)-propionic acid (14.87 g; 74.26% yield) having $[\alpha]_D^{23} = +342.98°$ to which corresponds a 99.13% optical purity.

EXAMPLE 3

By working in a way analogous to that described in example 1 but using a molar ratio of 0.5:1 for 1S,2S-thiomicamine and 0.5:1 for NaOH with respect to the derivative of the threo propionic acid the desired salt (27.06 g; 81.02% yield) was obtained with $[\alpha]_D^{23} = +306.05°$ (c=0.5% in $CH_3OH$).

The salt was treated as described in example 2 to give the (2S,3S)-threo-2-hydroxy-3-(2-aminophenylthio)-3-(4-methoxyphenyl)-propionic acid (14.45 g; 72% yield) with $[\alpha]_D^{23} = +340.65°$ to which corresponds a 98.45% optical purity.

EXAMPLE 4

The following example shows the resolution process starting from esters of the acid to be resolved.

Water (192 g) and flakes of sodium hydroxide (5.76 g) (97% titre; 0.14 mol) were introduced into a 250 ml flask equipped with mechanical stirrer, thermometer and reflux condenser.

The methyl ester of the threo-2-hydroxy-3-(2-aminophenylthio)-3-(4-methoxyphenyl)-propionic acid (40 g) as enantiomeric mixture (HPLC titre=99.7%) (0.12 mol) (threo/erythro=99/1) was added to the solution so obtained, under stirring at room temperature in 5 minutes.

The reaction mixture (suspension) was heated in 30 minutes to +50° C. (after 15 minutes at +50° C. the reaction mixture became a solution), then was kept under stirring at +50° C. for 45 minutes.

The reaction mixture was kept under stirring between +40° C. and +50° C. undcer vacuum (50 mmHg) for 0.5 hour to remove the volatile portion.

The alkaline aqueous solution so obtained (150 ml volume) was introduced in 2 l reactor equipped with mechanical stirring, termometer and reflux condenser.

The solution was diluted with water (1350 g), then was heated to +60° C. and was brought to pH 6.8 (measured at +60° C. with pHmetre) with an aqueous solution (17 g) containing hydrochloric acid (0.62 g; 0.017 mol). The solution was then heated up to 100° C.

A solution obtained mixing (S,S)-thiomicamine (10.2 g; 0.048 mol) with an aqueous solution (48 g) containing hydrochloric acid (1.75 g; 0.048 mol) was added in 15 minutes to the solution obtained as above, kept under stirring.

At the end of the dripping the solution was lightly cloudly.

The mixture was maintained at 100° C. until complete dissolution of the precipitate, then was cooled to +70° C. in 0.5 hour. At this temperature the optically pure thiomicamine salt (0.5 g) was seeded. It was observed the formation of the precipitate.

The mixture was cooled in 1.5 hours to +40° C., then it was filtered. The precipitate washed with water (100 g) and dried for one night under vacuum at 50° C. to give the (S,S)-thiomicamine salt (16 g) which was recrystallized from water.

1N HCL (10 ml) was added to a mixture of a portion of the salt so obtained (4.4 g; 10.0 mmol) and water (200 ml), kept under stirring at +100° c. After 0.5 hour the mixture was cooled up to room temperature and the precipitate was filtered, washed with water and dried for one night at 50° C. under vacuum (200 mmHg).

The (2S,3S)-threo-2-hydroxy-3-(2-aminophenylthio)-3-(4-methoxyphenyl)-propionic acid was obtained having $[\alpha]_D^{23} = +340°$ (c=0.35; EtOH) (e.e.=98.3%).

EXAMPLE 5

The following example shows the resolution process by using (1S,2S)-threo-2-amino-1-phenyl-1,3-propanediol.

Water (240 g) and flakes of sodium hydroxide (7.2 g) (97% titre; 0.18 mol) were introduced, in a nitrogen atmosphere, under stirring at room temperature in a 250 ml flask equipped with mechanical stirrer, termometer and reflux condenser.

The methyl ester of the threo-2-hydroxy-3-(2-aminophenylthio)-3-(4-methoxyphenyl)-propionic acid (50 g) (HPLC titre=99.7%) (0.15 mol) (threo/erythro=99/1) was added in 5 minutes to the solution so obtained, under stirring at room temperature.

The reaction mixture (suspension) was heated in 30 minutes to +50° C. (after 15 minutes at +50° C. the reaction mixture became a solution), then was kept under stirring at +50° C. for 45 minutes.

The reaction mixture was kept under stirring between +40° C. and +50° C. under vacuum (50 mmHg) for 0.5 hour to remove the volatile portion.

The alkaline aqueous solution so obtained (190 ml volume) was introduced in a 2 l reactor equipped with mechanical stirring, thermometer and reflux condenser and kept under nitrogen.

The solution was diluted with water (1680 g), then was heated to +60° C. and was brought to pH 6.6 (measured at +60° c. with pHmeter) with an aqueous solution (26 g) containing hydrochloric acid (0.95 g; 0.026 mol).

A solution obtained by mixing (1S,2S-threo-2-amino-2-phenyl-1,3-propanediol (10 g; 0.06 mol) with an aqueous solution (60 g) containing hydrochloric acid (2.19 g; 0.06 mol) was added in 15 minutes to the solution obtained as above, kept under stirring.

At the end of the dripping a slight cloudiness of the solution was observed.

The mixture was maintained at 100° C. until complete dissolution of the precipitate, then was gradually cooled up to 40° C. in 4 hours and kept at 25° C.–28° C. for 14 hours.

The precipitate so obtained was washed with water (150 g) and dried for one night under vacuum at 50° C. to give the L(+)-threo-2-amino-1-phenyl-1,3-propanediol salt of the threo-2-hydroxy-3-(2-aminophenylthio)-3-(4-methoxyphenyl)-propionic acid (21 g).

1N HCl (10 ml) was added to a mixture of the salt so obtained (4.9 g; 10.0 mmol) and water (300 ml), kept under stirring at +100° C. After 0.5 hour the mixture was cooled up to room temperature and the precipitate was filtered, washed with water and dried for one night at 50° C. under vacuum (200 mmHg).

The (2S,3S)-threo-2-hydroxy-3-(2-aminophenylthio)-3-(4-methoxyphenyl)-propionic acid was obtained having $[\alpha]_D^{23} = +300°$ (c=0.35; EtOH).

What is claimed is:

1. A process for the separation of the (2S, 3S)-threo enantiomer of 2-hydroxy-3-(2-aminophenylthio)-3-(4-methoxyphenyl)-propionic acid from a racemic mixture of it with the (2R, 3R)-threo enantiomer, comprising:
   heating up to complete dissolution of a mixture of: the racemic mixture; a resolving agent, (1S, 2S)-threo-1-aryl-2-amino-1,3-propanediol, of the formula

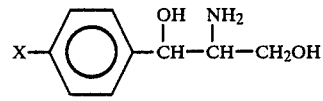

(I, threo 1S,2S)

wherein X is H, $CH_3S$, $NO_2$ or $CH_3SO_2$;
in an amount substantially in the molar ratio of 0.5 with respect to the mixture to be resolved;
   an alkaline hydroxide, in an amount substantially in the molar ratio of 0.5 with respect to the mixture to be resolved; and
   an aqueous or alcoholic-aqueous solvent;
slowly cooling the resulting solution to the temperature at which crystallization of the salt of (2S, 3S)-threo-2-hydroxy-3-(2-aminophenylthio)-3-(4-methoxyphenyl)-propionic acid with (1s, 2S)-threo-1-aryl-2-amino-1,3-propandiol begins; and
collecting the salt and, optionally, isolating the (2S, 3S)-threo-2-hydroxy-3-(2-aminophenylthio)-3-(4-methoxyphenyl)-propionic acid by treatment with a mineral acid in an aqueous environment.

2. A process according to the claim 1 in which the compound of formula I wherein X=$CH_3S$ is used as resolving agent.

3. A process according to claim 1 which the resolving agent is used in slight default.

4. A process according to the claim 1 in which the alkaline hydroxide is used in slight excess.

5. A process according to the claim 1 which the (2S,3S)-threo-2-hydroxy-3-(2-aminophenylthio)-3-(4-methoxyphenyl)-propionic acid is liberated from the salt with the compound I by treatment with aqueous mineral acids.

6. A process according to claim 3, wherein the resolving agent is used in a molar ratio of 0.45 with respect to the mixture to be resolved.

7. A process according to claim 4, wherein the alkaline hydroxide is used in a molar ratio of 0.55 with respect to the mixture to be resolved.

* * * * *

UNITED STATES PATENT AND TRADEMARK OFFICE
CERTIFICATE OF CORRECTION

PATENT NO. : 4,939,295

DATED : July 3, 1990

INVENTOR(S) : Claudio GIORDANO, et al

It is certified that error appears in the above-identified patent and that said Letters Patent is hereby corrected as shown below:

On the title page, Item --[75] insert before "Valeriano Merli" --Claudio Giordano, Monza--.

Signed and Sealed this

Third Day of December, 1991

Attest:

HARRY F. MANBECK, JR.

Attesting Officer

Commissioner of Patents and Trademarks